(12) United States Patent
Kirschman

(10) Patent No.: US 10,039,854 B2
(45) Date of Patent: Aug. 7, 2018

(54) AIR-SURFACE DISINFECTION SYSTEM, UNIT AND METHOD

(71) Applicant: David Louis Kirschman, Dayton, OH (US)

(72) Inventor: David Louis Kirschman, Dayton, OH (US)

(73) Assignee: Aerobiotix, Inc., Dayton, OH (US)

( * ) Notice: Subject to any disclaimer, the term of this patent is extended or adjusted under 35 U.S.C. 154(b) by 0 days.

(21) Appl. No.: 15/642,704

(22) Filed: Jul. 6, 2017

(65) Prior Publication Data

US 2017/0296691 A1    Oct. 19, 2017

Related U.S. Application Data

(63) Continuation of application No. 15/164,233, filed on May 25, 2016, now Pat. No. 9,764,054, which is a continuation of application No. 14/283,870, filed on May 21, 2014, now Pat. No. 9,433,693, and a continuation-in-part of application No. 13/838,367, filed on Mar. 15, 2013, now Pat. No. 9,457,119.

(60) Provisional application No. 61/826,145, filed on May 22, 2013, provisional application No. 61/735,623, filed on Dec. 11, 2012.

(51) Int. Cl.
| | | |
|---|---|---|
| *G01N 23/00* | (2006.01) | |
| *A61N 5/00* | (2006.01) | |
| *A62B 7/08* | (2006.01) | |
| *A61L 9/20* | (2006.01) | |
| *A61L 2/10* | (2006.01) | |
| *A61L 2/26* | (2006.01) | |

(52) U.S. Cl.
CPC .................... *A61L 9/20* (2013.01); *A61L 2/10* (2013.01); *A61L 2/26* (2013.01); *A61L 2202/11* (2013.01); *A61L 2202/14* (2013.01); *A61L 2202/16* (2013.01); *A61L 2202/25* (2013.01); *A61L 2209/11* (2013.01)

(58) Field of Classification Search
CPC ..................................... A61L 9/00; A61L 9/20
USPC .......... 422/5, 24, 121, 124–125; 250/455.11, 250/492.1
See application file for complete search history.

(56) References Cited

U.S. PATENT DOCUMENTS

| | | |
|---|---|---|
| 3,683,638 A | 8/1972 | Devon |
| 3,744,216 A | 7/1973 | Halloran |
| 3,804,942 A | 4/1974 | Kato et al. |

(Continued)

FOREIGN PATENT DOCUMENTS

| | | |
|---|---|---|
| DE | 19614893 | 10/1997 |
| EP | 1491218 | 12/2004 |
| WO | 0160419 | 8/2001 |

OTHER PUBLICATIONS

Mohammadian, "Effect of TiO2 Nanoparticles on the Spectral Characteristics of Rhodamine 6G Fluorescence Emission", Mar. 2012, ICNS4, All Pages.

*Primary Examiner* — Monzer R Chorbaji
(74) *Attorney, Agent, or Firm* — Jacox, Meckstroth & Jenkins

(57) ABSTRACT

A system, unit, device and method are shown for providing substantially simultaneous disinfection of bacteria or other pathogens in air passing through the system using C-band ultraviolet radiation from an ultraviolet light source and that is also capable of substantially simultaneous and efficient disinfecting air and surfaces outside the device using the same ultraviolet light source.

30 Claims, 4 Drawing Sheets

(56) References Cited

U.S. PATENT DOCUMENTS

| | | |
|---|---|---|
| 3,812,370 A | 5/1974 | LaViolette |
| 3,988,131 A | 10/1976 | Kanazawa et al. |
| 4,118,191 A | 10/1978 | Bohnensieker |
| 4,210,429 A | 7/1980 | Golstein |
| 4,225,323 A | 9/1980 | Zarchy et al. |
| 4,244,710 A | 1/1981 | Burger |
| 4,437,007 A | 3/1984 | Koslow et al. |
| 4,531,956 A | 7/1985 | Haworth |
| 4,621,195 A | 11/1986 | Larsson |
| 4,694,179 A | 9/1987 | Lew et al. |
| 4,737,173 A | 4/1988 | Kudirka et al. |
| 4,749,385 A | 6/1988 | Brunner et al. |
| 4,750,917 A | 6/1988 | Fujii |
| 4,787,922 A | 11/1988 | Kulitz |
| 4,835,983 A | 6/1989 | Chandler, Jr. et al. |
| 4,900,344 A | 2/1990 | Lansing |
| 4,954,320 A | 9/1990 | Birmingham et al. |
| 4,959,010 A | 9/1990 | Burtscher et al. |
| 4,990,313 A | 2/1991 | Pacosz |
| 5,004,483 A | 4/1991 | Eller et al. |
| 5,225,167 A | 7/1993 | Wetzel |
| 5,233,975 A | 8/1993 | Choate |
| 5,240,478 A | 8/1993 | Messina |
| 5,399,319 A | 3/1995 | Schoenberger et al. |
| 5,601,786 A | 2/1997 | Monagan |
| 5,616,172 A | 4/1997 | Tuckerman et al. |
| 5,616,532 A | 4/1997 | Heller et al. |
| 5,656,242 A | 8/1997 | Morrow et al. |
| 5,681,374 A | 10/1997 | Von Glehn |
| 5,761,908 A | 6/1998 | Oas et al. |
| 5,772,738 A | 6/1998 | Muraoka |
| 5,891,399 A * | 4/1999 | Owesen ............... A61L 9/20 422/121 |
| 5,997,619 A | 12/1999 | Knuth et al. |
| 6,053,968 A | 4/2000 | Miller |
| 6,182,461 B1 | 2/2001 | Washburn et al. |
| 6,248,235 B1 | 6/2001 | Scott |
| 6,322,614 B1 | 11/2001 | Tillmans |
| 6,544,485 B1 | 4/2003 | Taylor |
| 6,613,277 B1 | 9/2003 | Monagan |
| 6,656,424 B1 | 12/2003 | Deal |
| 6,797,042 B2 | 9/2004 | LaFerriere et al. |
| 6,911,177 B2 | 6/2005 | Deal |
| 7,251,953 B2 | 8/2007 | Wetzel et al. |
| 7,318,856 B2 | 1/2008 | Taylor et al. |
| 7,323,065 B2 | 1/2008 | Fend et al. |
| 7,531,141 B2 | 5/2009 | Descotes et al. |
| 7,854,900 B2 | 12/2010 | Takeda et al. |
| 7,892,501 B2 | 2/2011 | Parker et al. |
| 8,168,122 B2 | 5/2012 | Lee |
| 8,236,236 B2 | 8/2012 | Garner |
| 8,252,099 B2 | 8/2012 | Worrilow |
| 2002/0085947 A1 | 7/2002 | Deal |
| 2002/0144601 A1 | 10/2002 | Palestro et al. |
| 2002/0172627 A1 * | 11/2002 | Aoyagi ............... B01D 53/885 422/179 |
| 2003/0012703 A1 | 1/2003 | Lee |
| 2003/0086831 A1 | 5/2003 | Horton |
| 2003/0198568 A1 | 10/2003 | Fend |
| 2005/0000365 A1 | 1/2005 | Nelsen et al. |
| 2006/0057020 A1 | 3/2006 | Tufo |
| 2007/0041882 A1 | 2/2007 | Roseberry et al. |
| 2009/0041617 A1 | 2/2009 | Lee |
| 2009/0041632 A1 | 2/2009 | Day et al. |
| 2012/0183443 A1 | 7/2012 | Hurley |
| 2012/0183444 A1 | 7/2012 | Lee |
| 2012/0282135 A1 | 11/2012 | Trapani |
| 2014/0044590 A1 | 2/2014 | Trapani |
| 2014/0154133 A1 | 6/2014 | Lee |

* cited by examiner

AIR-SURFACE DISINFECTION SYSTEM, UNIT AND METHOD

CROSS-REFERENCE TO RELATED APPLICATIONS

The present application is a continuation of U.S. application Ser. No. 15/164,233, filed May 25, 2016, which is a continuation of U.S. application Ser. No. 14/283,870, filed May 21, 2014, now issued as U.S. Pat. No. 9,433,693, which claims priority to provisional U.S. Application Ser. No. 61/826,145, filed May 22, 2013, and which is also a continuation-in-part of U.S. application Ser. No. 13/838,367, filed Mar. 15, 2013, now issued as U.S. Pat. No. 9,457,119, which claims priority to provisional U.S. Application Ser. No. 61/735,623, filed Dec. 11, 2012, all of which Applicant claims the benefit of the earliest filing date. These applications are incorporated herein by reference and made a part hereof.

BACKGROUND OF THE INVENTION

1. Field of the Invention

This invention relates to disinfection and, more particularly, to disinfection of airborne bacteria or other pathogens and substantially simultaneous surface disinfection.

2. Description of the Related Art

Recently, there has been increased interest in surface and air disinfection, particularly in health care settings. A number of devices have been developed which use C-band ultraviolet light (UVC) and have shown some success in decontaminating surfaces within a room. Devices typically consist of multiple UVC lamps arranged in a circular pattern and projecting UVC radiation onto exposed surfaces of a room. These devices are typically mobile and can be wheeled into position as needed.

There has also been interest in the health care industry to provide air disinfection, as airborne bacteria and other pathogens have shown to cause hospital-acquired infections. A number of air purification systems have been developed to address this issue.

Because both air and surface disinfection are important, what is needed and would be beneficial is to provide a device which is capable of simultaneously and efficiently disinfecting air and surfaces within a room, using the same UVC source.

SUMMARY OF THE INVENTION

One object of the invention is to provide a system and method that is capable of substantially simultaneous and efficient disinfection of both air and surfaces within a room using the same ultraviolet light source.

Another object of the invention is to provide a system and method that supports a plurality of ultraviolet lamps or light sources about a transparent tubular member.

Still another object of the invention is to provide a system and method that utilize a majority of light rays emitted from an ultraviolet light source to disinfect, such as using some of the light rays to disinfect air passing through an interior of a generally circular transparent member that defines a passageway surrounded by an array of the plurality of ultraviolet light sources and that causes outwardly-projecting rays to disinfect surrounding surfaces outside the passageway.

Still another object of one embodiment of the invention is to provide a transparent tubular member having an array of a plurality of ultraviolet light sources situated there around so that light can pass through the transparent tubular member to disinfect air passing there through and other light rays from the plurality of ultraviolet light sources substantially simultaneously disinfect at least one or a plurality of surfaces in a room where the plurality of ultraviolet light sources are located.

Still another object of one embodiment of the invention is to provide a transparent tubular member for use in a disinfection system and method that is hollow or can be filled with reflective, focusing, concentrating or baffling apparatus to slow or create turbulence within the airflow or otherwise improve ultraviolet effective.

In one aspect, one embodiment of the invention comprises a disinfection unit comprising a housing comprising a blower or fan for blowing air, a transparent tubular member for receiving air blown by the blower or fan and for directing it in a predetermined direction, a plurality of ultraviolet light sources supported by the housing and arranged in a predetermined pattern around the transparent tubular member such that, when the plurality of ultraviolet light sources are energized, the plurality of ultraviolet light sources projecting ultraviolet radiation outward to facilitate sterilizing an environment outside the housing, the plurality of ultraviolet light sources also projecting ultraviolet radiation through the transparent tubular member to facilitate sterilizing air blown through the transparent tubular member, and a controller coupled to the blower or fan and the plurality of ultraviolet light sources for controlling operation of the disinfection unit.

In another aspect, another embodiment of the invention comprises an air-surface disinfector comprising a transparent tubular member defining a passageway for receiving air and for directing the air in a predetermined direction and a plurality of ultraviolet light sources arranged in a predetermined pattern such that, when the plurality of ultraviolet light sources are energized, ultraviolet radiation is projected inwardly through the transparent tubular member to facilitate sterilizing air passing through the transparent tubular member and outwardly to facilitate sterilizing an environment or area around the plurality of ultraviolet light sources.

In still another aspect, another embodiment of the invention comprises a method for disinfecting an area or environment, the method comprising the steps of arranging a plurality of ultraviolet light sources in a predetermined order such that they generally surround a predetermined interior disinfecting area, directing infected air through the predetermined interior disinfecting area, energizing the plurality of ultraviolet light sources so that they radiate the predetermined interior disinfecting area and disinfect the infected air that passes therethrough, the plurality of ultraviolet light sources generating ultraviolet light that radiates away from the predetermined interior disinfecting area to also disinfect air surrounding the plurality of ultraviolet light sources and at least one surface in the area or environment in which the plurality of ultraviolet light sources are energized.

This invention, including all embodiments shown and described herein, could be used alone or together and/or in combination with one or more of the features covered by one or more of the following list of features:

The disinfection unit wherein the environment comprises at least one surface, the ultraviolet radiation comprising an intensity adapted to disinfect the at least one surface.

The disinfection unit wherein the at least one surface is at least one of a surface of furniture or an interior surface of a medical room or hospital room.

The disinfection unit wherein the predetermined pattern comprises a generally circular pattern arranged around the transparent tubular member.

The disinfection unit wherein the transparent tubular member is generally cylindrical.

The disinfection unit wherein the plurality of ultraviolet light sources are elongated and each have an axis that is generally parallel to an axis of the transparent tubular member.

The disinfection unit wherein the disinfection unit comprises an end cap grate through which air may pass; the end cap being associated with first ends of the plurality of ultraviolet light sources and adapted to retain the plurality of ultraviolet light sources in an upright and spaced relationship.

The disinfection unit wherein the transparent tubular member is silicate quartz.

The disinfection unit wherein the transparent tubular member comprises a first end situated on the housing in operative relationship to the blower or fan, the blower or fan drawing air in from a base of the housing and expelling it through an exit opening of the transparent tubular member.

The disinfection unit wherein the predetermined direction is generally vertical and upward.

The disinfection unit wherein the disinfection unit comprises at least one baffle or airflow interrupter for interrupting the air flowing through the transparent tubular member to facilitate improving ultraviolet radiation effectiveness.

The disinfection unit wherein the at least one baffle or airflow interrupter comprises a plurality of quartz tubular members.

The disinfection unit wherein the plurality of ultraviolet light sources are elongated lamps emitting C-band radiation.

The air-surface disinfector wherein the environment or area comprises at least one surface, the ultraviolet radiation comprising an intensity adapted to disinfect the at least one surface.

The air-surface disinfector wherein the at least one surface is at least one of a surface of a medical room or hospital room or furniture located therein.

The air-surface disinfector wherein the predetermined pattern comprises a generally circular pattern arranged around the transparent tubular member.

The air-surface disinfector wherein the transparent tubular member is generally cylindrical.

The air-surface disinfector wherein the plurality of ultraviolet light sources are elongated and each have an axis that is generally parallel to an axis of the transparent tubular member.

The air-surface disinfector wherein the air-surface disinfector comprises an end cap grate through which air may pass; the end cap grate being associated with first ends of the plurality of ultraviolet light sources and adapted to retain the plurality of ultraviolet light sources in an upright and spaced relationship and in operative relationship to the transparent tubular member.

The air-surface disinfector wherein the transparent tubular member is silicate quartz.

The air-surface disinfector wherein the transparent tubular member comprises a first end situated on a housing in operative relationship to a blower or fan, the blower or fan drawing air in from a base of the housing and expelling it through an exit opening of the transparent tubular member.

The air-surface disinfector wherein the predetermined direction is generally vertical and upward.

The air-surface disinfector wherein the air-surface disinfector comprises at least one baffle or airflow interrupter for interrupting the air flowing through the transparent tubular member to facilitate improving ultraviolet radiation effectiveness.

The air-surface disinfector wherein the at least one baffle or airflow interrupter comprises a plurality of quartz tubular members situate in the transparent tubular member.

The air-surface disinfector wherein the plurality of ultraviolet light sources are elongated lamps emitting C-band radiation.

The method for disinfecting an area or environment wherein the plurality of ultraviolet light sources are elongated lamps, the method further comprises the step of arranging the plurality of ultraviolet light sources in a generally circular pattern.

The method for disinfecting an area or environment wherein the plurality of ultraviolet light sources are elongated tubular ultraviolet lamps, the arranging step further comprising the step of arranging the plurality of ultraviolet light sources around a transparent tubular member that defines the predetermined interior disinfecting area.

The method for disinfecting an area or environment wherein the transparent tubular member is silicate quartz.

The method for disinfecting an area or environment wherein the plurality of ultraviolet light sources are elongated ultraviolet lamps, the method further comprising the step of arranging the plurality of ultraviolet light sources so that their axes are generally vertical with respect to the ground.

The method for disinfecting an area or environment wherein axes of the plurality of ultraviolet light sources are elongated ultraviolet lamps, the method further comprising the step of arranging the plurality of ultraviolet light sources such that their axes are generally parallel to an axis of the transparent tubular member.

The method for disinfecting an area or environment wherein the plurality of ultraviolet light sources comprise a plurality of elongated lamps that are arranged in an upright and generally circular plan.

The method for disinfecting an area or environment wherein the plurality of ultraviolet light sources project light in a first direction into the predetermined interior disinfecting area and also in a second direction that is generally opposite the first direction, the light in the second direction being substantially uninterrupted until it encounters at least one surface, the at least one surface becoming substantially disinfected in response to the light.

These and other objects and advantages of the invention will be apparent from the following description, the accompanying drawings and the appended claims.

DETAILED DESCRIPTION OF PREFERRED EMBODIMENTS

Figure 1:
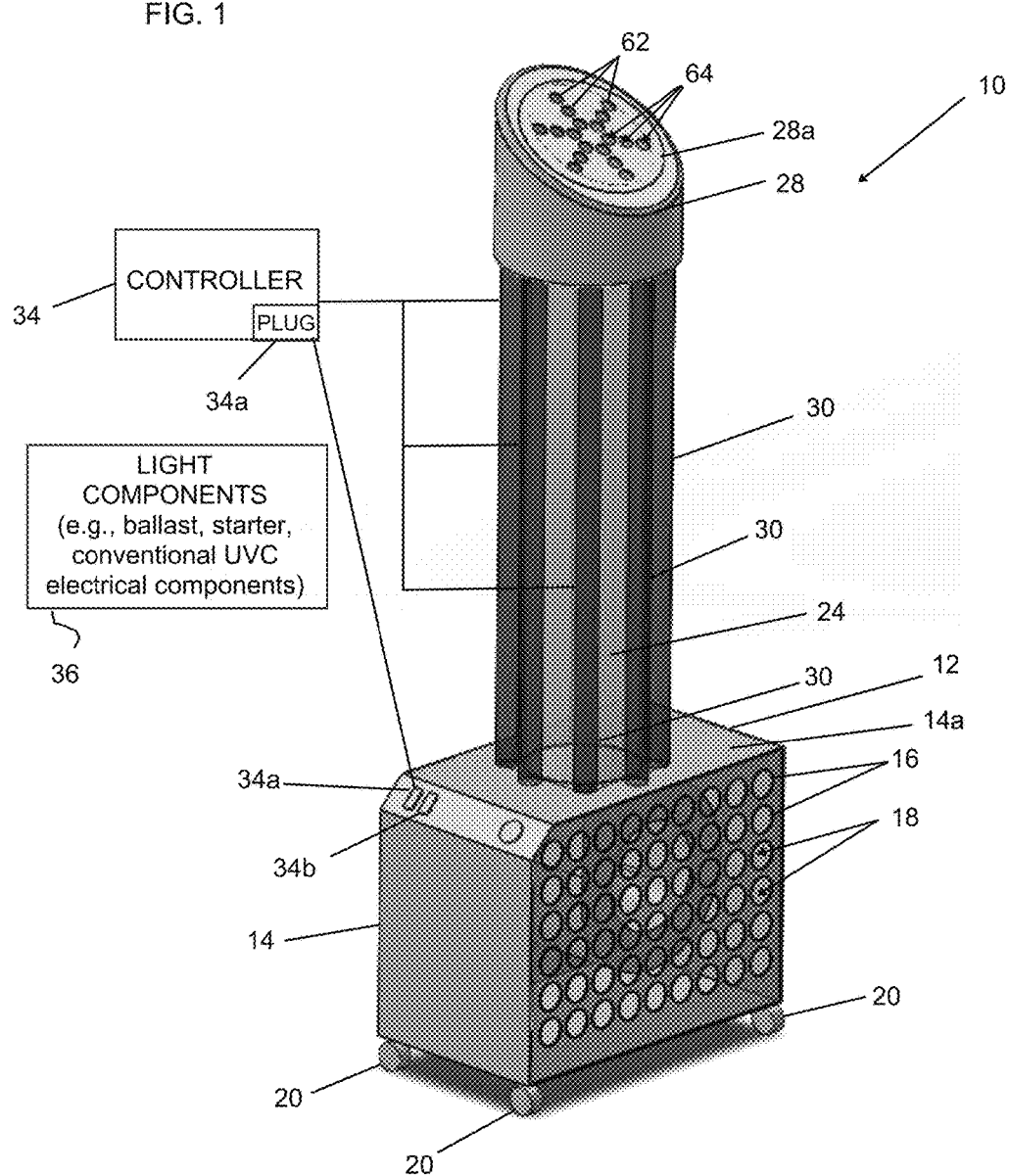
FIG. 1 is perspective view of a disinfection unit, system and method for disinfecting both air passing through the system and also disinfecting surfaces in an environment surrounding the system.

Referring now to FIGS. 1-4, a disinfection system, air-surface disinfector and method are shown. The disinfection system 10 comprises a disinfection unit or disinfector 12 having a housing 14. The housing 14 comprises at least one or a plurality of interior generally circular walls 16 that define a plurality of perforations or ventilation openings or holes 18 in the housing 14. Although not shown, a plurality of sides of the housing 14 may comprise the ventilation openings or holes 18.

The housing 14 further comprises a plurality of wheels or castors 20 that enable the disinfection system 10 to be mobile and moveable from one area to another.

The disinfection system 10 further comprises a blower or fan 22 (best illustrated in FIGS. 3 and 4) that is conventionally mounted in the housing 14. In one embodiment, the blower or fan 22 is a radial fan having an inlet 22a and an outlet or exit 22b (FIG. 4). The disinfection system 10 further comprises a transparent tubular member 24 having a first end 24a that is received and supported on the sleeve or exit duct 22c of the blower or fan 22 and supported thereon. In the illustration being described, the transparent tubular member 24 comprises a tube axis TA (FIG. 4). The transparent tubular member 24 defines a passageway 27 that defines a predetermined interior disinfection area for receiving air blown by the blower or fan 22 and for directing it toward the outlet or exit 22b and through an end cap or grate 28 that will be described in more detail later herein.

Notice that the disinfection system 10 comprises a plurality of ultraviolet light sources 30 that are arranged in a predetermined pattern around the transparent tubular member 24 as shown. When the plurality of ultraviolet light sources 30 are energized, they provide C-band ultraviolet radiation that disinfects the air passing or blown through the passageway 27 as will be described in more detail later herein.

In the illustration being described, the plurality of ultraviolet light sources 30 each comprised an elongated ultraviolet lamp, such as an ultraviolet lamp 32 illustrated in FIG. 4. For ease of description and understanding, FIG. 4 illustrates a single ultraviolet lamp 32 and its relationship to the transparent tubular member 24, but it should be understood that the plurality of the ultraviolet lamps 32 surround the transparent tubular member 24 in a generally circular array as mentioned. Although the plurality of ultraviolet light sources 30 are each shown as including the elongated ultraviolet lamp 32, it should be appreciated that other ultraviolet light sources could be used.

The disinfection system 10 further comprises a controller 34 for controlling an operation of the disinfection system 10. In the illustration being described, the controller 34 is electrically coupled to the blower or fan 22, the plurality of ultraviolet light sources 30 and various conventional light components 36, which include, for example, a ballast 46 (FIG. 4), starter, conductors and lamp holders. The light components 36 are mounted in or on the housing 14 and under the control of the controller 34.

As best illustrated in FIG. 4, note that the light components 36 comprise a first lamp holder 40 mounted on a surface 14a of the housing 14 and a second lamp holder 42 that is mounted on an interior surface 44a of a generally radial wall 44 of the grate 28. It should be understood that each of the plurality of ultraviolet light sources 30 are supported between a pair of lamp holders 40 and 42 so that a lamp axis LA of each of the plurality of ultraviolet light sources 30 is generally parallel to the axis TA as illustrated in FIG. 4. The lamp holders 40 and 42 comprise conventional bi-pin female connectors, such as connectors 40a in FIG. 4, that each receives a conductive pin 30a of the ultraviolet light source 30. For ease of illustration, the lamp holders 40 and 42 are mounted on the housing 14 and the interior surface 44a of the grate 28. As mentioned, the lamp holders 40 and 42 are conventional and comprise the conventional connectors, such as connectors 40a, which are electrically coupled together by wires (not shown) and to a ballast 46 which in turn is coupled to the controller 34. Other conventional UVC components (not shown) may be used.

As mentioned, the light components 36 (FIG. 1) comprise the conventional components, such as ballast, starter, electrical conductors, lamps holders and the like, that are adapted and fitted to the disinfection system 10 in order to support the plurality of ultraviolet light sources 30 in a generally upright and vertical position and adjacent to the transparent tubular member 24 as shown in FIG. 4.

The disinfection system 10 further comprises an electrical plug 34a (FIG. 1) that is coupled to a conventional power source, such as a conventional 120 volt AC power source. It should be understood, however, that the housing 14 could comprise a conventional DC power source, such as a 6 volt or 12 volt DC battery, for operating the components of the disinfection system 10.

Referring back to FIG. 4, the lamp holder 40 is conventionally mounted to the surface 14a, and the lamp holder 42 is conventionally mounted to the interior surface 44a of wall 44 of the end cap or grate 28.

During operation, C-band ultraviolet light is emitted from each of the plurality of ultraviolet light sources 30 so that a portion of the light, such as the rays labeled IR in FIG. 4, are transmitted through the transparent tubular member 24 and into the passageway 27 where infected air passes therethrough. The radiation disinfects the air passing through the passageway 27. Note, however, that other light rays, labeled OR in FIG. 4, are transmitted outside to the surrounding environment 26 to disinfect the air surrounding the disinfection system 10 and also disinfect at least one or a plurality of surfaces in the environment 26.

Advantageously, the disinfection system 10 simultaneously and efficiently disinfects the air passing through the transparent tubular member 24 and passageway 27 as well as at least one or a plurality of surfaces within a room. In this regard, the at least one or a plurality of surfaces may be a wall surface, a ceiling surface, a floor surface, fixtures, such as a sink or toilet surfaces, or furniture, such as a chair, table, bed or the like. These various elements are labeled and shown as part number 26 in FIG. 3.

Figure 2:
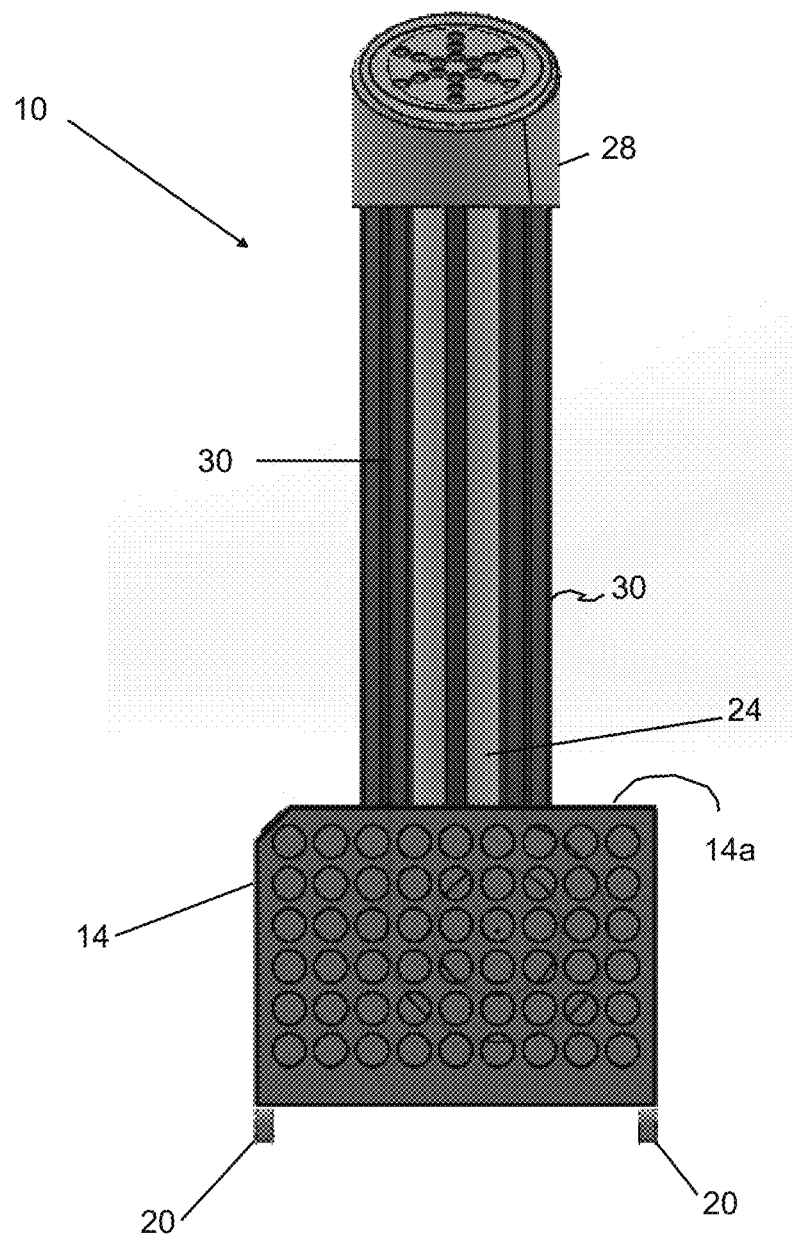
FIG. 2 is another view of the system shown in FIG. 1 illustrating the ventilation holes in a housing that supports the components of the system and also showing an end cap or grate which also has exit ventilation holes.
Figure 3:
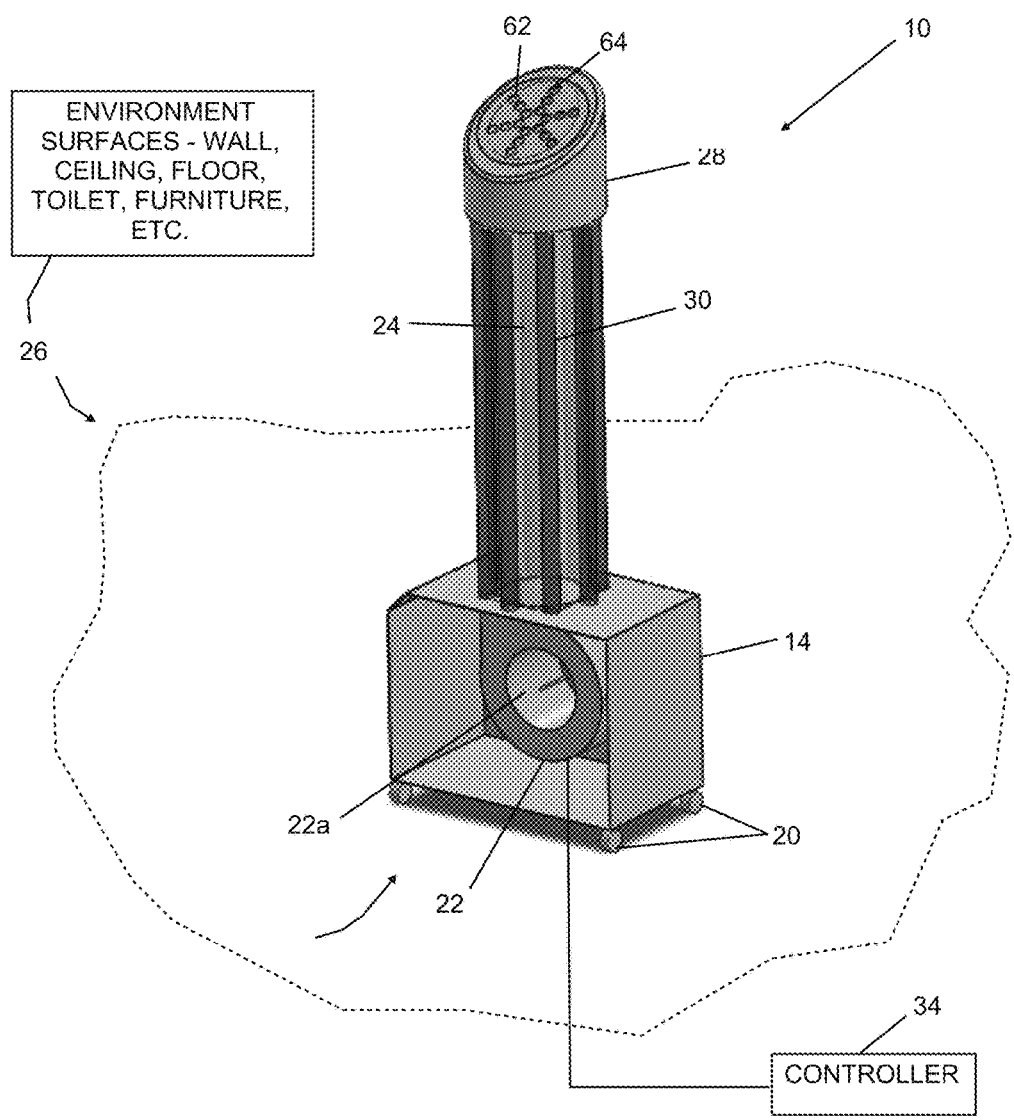
FIG. 3 is a perspective view of the ventilation system shown in FIGS. 1 and 2 with the end cap or grate removed so that the internal blower or fan may be seen.
Figure 4:
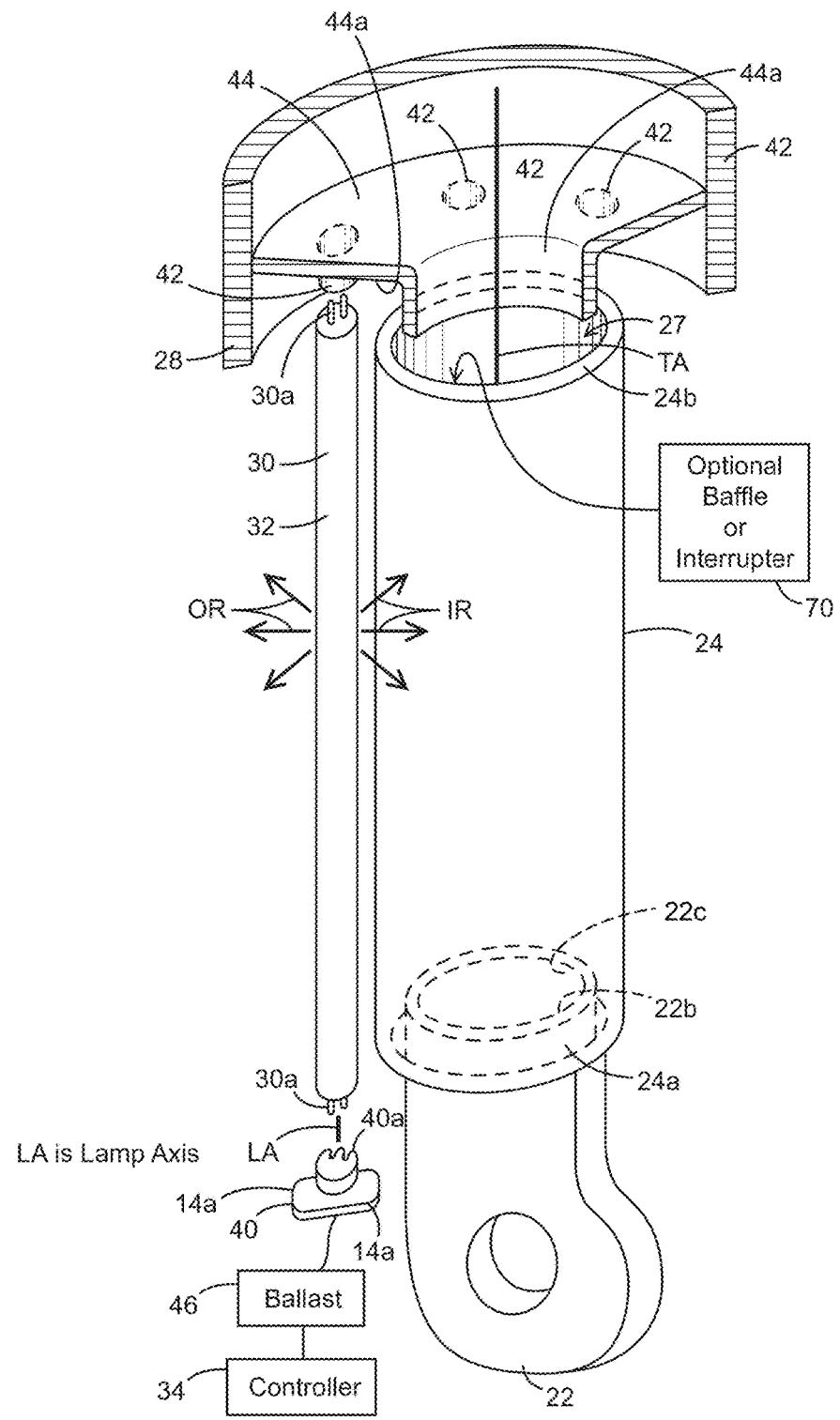
FIG. 4 is a fragmentary and sectional view illustrating a blower or fan shown in FIG. 3 supporting a first or input end of a transparent tubular member and portions of the end cap or grate which has a generally circular wall that supports a second or exit end of the transparent tubular member and further showing lamp holders in the end cap or grate and on a surface of the housing for supporting a plurality of ultraviolet light sources in a generally parallel relationship with each other and with the transparent tubular member.

Referring back to FIG. 4, note that the end cap or grate 28 has a generally planar exit surface 28a having a plurality of interior circular walls 62 that define a plurality of ventilation holes or openings 64 as illustrated in FIGS. 1-3 in order to direct air general upward and in a predetermined direction after the air exits the end 24b of the transparent tubular member 24. Note that the end cap or grate 28 also serves the function of supporting the transparent tubular member 24 and the plurality of ultraviolet light sources 30 generally vertically and upright as illustrated in FIG. 4. In this regard, the end cap or grate 28 has the interior generally radial wall 44 with the interior surface 44a onto which the lamp holders 42 are mounted as shown. The generally radial wall 44 comprises an interior surface 44a that is received inside the passageway 27 at the end 24b of the transparent tubular member 24. The interior surface 44a is generally circular and is adapted and sized to be received in the transparent tubular member 24 in order to support it in the generally upright position illustrated in the figures. For ease of illustration, the end cap or grate 28, walls 44 and interior surface 44a are illustrated in a sectional and fragmentary view so that the various components of the end cap or grate 28 may be seen.

During use, a user moves the disinfection system 10 into a predetermined environment, such as the environment 26 (FIG. 3), which may be, for example, an interior environment of a building such as a hospital room, medical room, home or other area where it is desired to disinfect air in the environment 26 and at least one surface in the environment 26. The disinfection system 10 is plugged into a power source via electrical plug 34a (FIG. 1). The user may actuate a switch 34b which causes controller 34 to energize the plurality of ultraviolet light sources 30 and the blower or fan 22. Air passes through the ventilation openings or holes 18 in the housing 14 and into the radial blower or fan 22. The air is blown through the passageway 27 of the transparent tubular member 24 along the axis TA and through the end 24b of the transparent tubular member 24. As the air passes through passageway 27 defined by the transparent tubular member 24, the ultraviolet light rays IR (FIG. 4) irradiate the air and facilitate killing unwanted bacteria and pathogens. Substantially simultaneously, the light rays OR irradiate the at least one surface in the environment 26 and the surrounding air, thereby disinfecting the at least one surface which may include the surfaces mentioned earlier herein.

As best illustrated in FIG. 4, the transparent tubular member 24 may be hollow and define the passageway 27, but alternatively, it could be filled with reflective, focusing, concentrating or baffling apparatus or airflow interrupter 70 to slow or create turbulence within the airflow passing through the passageway 27 in order to improve the ultraviolet effectiveness. For example, features of the system and devices of U.S. Ser. No. 13/838,367 filed Mar. 15, 2013, now issued as U.S. Pat. No. 9,457,119, which claims priority to provisional U.S. Application Ser. No. 61/735,623, filed Dec. 11, 2012, may be used, as well as U.S. application Ser. No. 15/164,233, filed May 25, 2016, which is a continuation of U.S. application Ser. No. 14/283,870, filed May 21, 2014, now issued as U.S. Pat. No. 9,433,693, which claims priority to provisional U.S. Application Ser. No. 61/826,145, filed May 22, 2013, and which is also a continuation-in-part of U.S. application Ser. No. 13/838,367, filed Mar. 15, 2013, all of which Applicant claims the benefit of the earliest filing date. These applications are owned by the same Assignee as the present application and are incorporated herein by reference and made a part hereof. Such features may include providing the at least one baffle or airflow interrupter 70 (FIG. 4). For example, the at least one baffle or airflow interrupter 70 may comprise a plurality of tubular quartz members (not shown) that are situated in the passageway 27.

As mentioned earlier, each of the plurality of ultraviolet light sources 30 comprises an elongated ultraviolet lamp member that uses C-band ultraviolet light (UVC), but other types of radiation could be used, such as A, B band ultraviolet, infrared, microwave, ionizing radiation, gamma radiation and the like.

Advantageously, the disinfection system 10, device and method provide simultaneous and efficient disinfection of air and surfaces within a room using the same plurality of ultraviolet light sources 30. Among other advantages, this reduces or eliminates the need for multiple disinfection units, such as an air-disinfection unit and a separate surface-disinfection unit.

This invention, including all embodiments shown and described herein, could be used alone or together and/or in combination with one or more of the features covered by one or more of the claims set forth herein, including but not limited to one or more of the features or steps mentioned in the Summary of the Invention and the claims.

While the system, apparatus and method herein described constitute preferred embodiments of this invention, it is to be understood that the invention is not limited to this precise system, apparatus and method, and that changes may be made therein without departing from the scope of the invention which is defined in the appended claims.

What is claimed is:

1. A disinfection unit comprising:
a housing comprising a blower or fan for blowing air;
a transparent tubular member for receiving air blown by said blower or fan and for directing it in a predetermined direction;
at least one ultraviolet light source supported by said housing and arranged in operative relationship with said transparent tubular member such that, when said at least one ultraviolet light source is energized, said at least one ultraviolet light source projecting ultraviolet radiation outward to facilitate sterilizing an environment outside said housing, said at least one ultraviolet light source also projecting ultraviolet radiation through said transparent tubular member to facilitate sterilizing air blown through said transparent tubular member; and
wherein said environment comprises at least one surface, said ultraviolet radiation comprising an intensity adapted to disinfect at least a portion of said air that flows through said transparent tubular member and substantially simultaneously disinfect said at least one surface situated outside said housing and in said environment;
a controller coupled to said blower or fan and said at least one ultraviolet light source for controlling operation of the disinfection unit;
wherein said air flows generally linearly over a substantial length of said transparent tubular member;
wherein said transparent tubular member comprises a tube axis, an inlet and an outlet and a passageway that defines a predetermined interior disinfection area for receiving air blown by said blower or fan, said transparent tubular member being generally tubular throughout its length from said inlet to said outlet and said blower or fan blowing or directing said air into said inlet and through said predetermined interior disinfection area and to said outlet where said air exits, said air being subjected to ultraviolet radiation while passing through said interior disinfection area until it passes through said outlet in a direction substantially coaxial with said tube axis or generally parallel thereto.

2. The disinfection unit as recited in claim 1 wherein said at least one surface is at least one of a surface of furniture or an interior surface of a medical room or hospital room.

3. The disinfection unit as recited in claim 1 wherein said at least one ultraviolet light source comprises a plurality of ultraviolet light sources and are arranged around said transparent tubular member in a predetermined pattern.

4. The disinfection unit as recited in claim 3 wherein said predetermined pattern comprises a generally circular pattern arranged around said transparent tubular member.

5. The disinfection unit as recited in claim 4 wherein said transparent tubular member is silicate quartz.

6. The disinfection unit as recited in claim 1 wherein said transparent tubular member is generally cylindrical.

7. The disinfection unit as recited in claim 6 wherein said transparent tubular member is silicate quartz.

8. The disinfection unit as recited in claim 1 wherein said at least one ultraviolet light source is elongated and has an axis that is generally parallel to an axis of said transparent tubular member.

9. The disinfection unit as recited in claim 1 wherein said disinfection unit comprises an end cap grate through which air may pass; said end cap being associated with first ends of said at least one ultraviolet light source and adapted to retain said at least one ultraviolet light source in an upright and spaced relationship.

10. The disinfection unit as recited in claim 1 wherein said transparent tubular member is silicate quartz.

11. The disinfection unit as recited in claim 1 wherein said transparent tubular member comprises a first end situated on said housing in operative relationship to said blower or fan, said blower or fan drawing air in from a base of said housing and expelling it through an exit opening of said transparent tubular member.

12. The disinfection unit as recited in claim 1 wherein said predetermined direction is generally vertical and upward.

13. The disinfection unit as recited in claim 1 wherein said disinfection unit comprises at least one baffle or airflow interrupter for interrupting said air flowing through said transparent tubular member to facilitate improving ultraviolet radiation effectiveness.

14. The disinfection unit as recited in claim 1 wherein said at least one ultraviolet light source is an elongated lamp emitting C-band radiation.

15. A disinfection unit comprising:
a housing comprising a blower or fan for blowing air;
a transparent tubular member for receiving air blown by said blower or fan and for directing it in a predetermined direction;
at least one ultraviolet light source supported by said housing and arranged in a predetermined pattern around said transparent tubular member such that, when said at least one ultraviolet light source is energized, said at least one ultraviolet light source projects ultraviolet radiation outward to facilitate sterilizing an environment outside said housing, said at least one ultraviolet light source also projecting ultraviolet radiation through said transparent tubular member to facilitate sterilizing air blown through said transparent tubular member; and
a controller coupled to said blower or fan and said at least one ultraviolet light source for controlling operation of the disinfection unit;
wherein said disinfection unit comprises at least one baffle or airflow interrupter for interrupting said air flowing through said transparent tubular member to facilitate improving ultraviolet radiation effectiveness;
wherein said at least one baffle or airflow interrupter comprises a plurality of quartz tubular members.

16. An air-surface disinfector comprising:
a transparent tubular member defining a passageway for receiving air and for directing said air in a predetermined direction; and
at least one ultraviolet light source arranged in operative relationship with said transparent tubular member such that, when said at least one ultraviolet light source is energized, ultraviolet radiation is projected inwardly through said transparent tubular member to facilitate sterilizing air passing through said transparent tubular member and outwardly to facilitate sterilizing an environment or area around said at least one ultraviolet light source;
wherein said environment comprises at least one surface, said ultraviolet radiation comprising an intensity adapted to disinfect at least a portion of said air that flows through said transparent tubular member and substantially simultaneously disinfect said at least one surface situated outside a housing and in said environment;
wherein said air flows generally linearly over a substantial length of said transparent tubular member;
wherein said transparent tubular member comprises a tube axis, an inlet and an outlet and a passageway that defines a predetermined interior disinfection area for receiving air blown by a blower or fan, said transparent tubular member being generally tubular throughout its length from said inlet to said outlet and said blower or fan blowing or directing said air into said inlet and through said predetermined interior disinfection area and to said outlet where said air exits, said air being subjected to ultraviolet radiation while passing through said interior disinfection area until it passes said outlet in a direction substantially coaxial with said tube axis or generally parallel thereto.

17. The air-surface disinfector as recited in claim 16 wherein said at least one surface is at least one of a surface of a medical room or hospital room or furniture located therein.

18. The air-surface disinfector as recited in claim 16 wherein said at least one ultraviolet light source comprises a plurality of ultraviolet light sources and are arranged around said transparent tubular member in a predetermined pattern.

19. The air-surface disinfector as recited in claim 18 wherein said predetermined pattern comprises a generally circular pattern arranged around said transparent tubular member.

20. The air-surface disinfector as recited in claim 16 wherein said transparent tubular member is silicate quartz.

21. The air-surface disinfector as recited in claim 16 wherein said transparent tubular member is generally cylindrical.

22. The air-surface disinfector as recited in claim 21 wherein said transparent tubular member is silicate quartz.

23. The air-surface disinfector as recited in claim 16 wherein said at least one ultraviolet light source is elongated and has an axis that is generally parallel to an axis of said transparent tubular member.

24. The air-surface disinfector as recited in claim 16 wherein said air-surface disinfector comprises an end cap grate through which air may pass; said end cap grate being associated with first ends of said at least one ultraviolet light source and adapted to retain said at least one ultraviolet light source in an upright and spaced relationship and in operative relationship to said transparent tubular member.

25. The air-surface disinfector as recited in claim 16 wherein said transparent tubular member is silicate quartz.

26. The air-surface disinfector as recited in claim 16 wherein said transparent tubular member comprises a first end situated on a housing in operative relationship to a blower or fan, said blower or fan drawing air in from a base of said housing and expelling it through an exit opening of said transparent tubular member.

27. The air-surface disinfector as recited in claim 16 wherein said predetermined direction is generally vertical and upward.

28. The air-surface disinfector as recited in claim 16 wherein said air-surface disinfector comprises at least one baffle or airflow interrupter for interrupting said air flowing through said transparent tubular member to facilitate improving ultraviolet radiation effectiveness.

29. The air-surface disinfector as recited in claim 16 wherein said at least one ultraviolet light source is an elongated lamp emitting C-band radiation.

30. An air-surface disinfector comprising:
a transparent tubular member defining a passageway for receiving air and for directing said air in a predetermined direction; and
at least one ultraviolet light source arranged in a predetermined pattern such that, when said at least one ultraviolet light source is energized, ultraviolet radiation is projected inwardly through said transparent tubular member to facilitate sterilizing air passing through said transparent tubular member and outwardly to facilitate sterilizing an environment or area around said at least one ultraviolet light source;
wherein said air-surface disinfector comprises at least one baffle or airflow interrupter for interrupting said air flowing through said transparent tubular member to facilitate improving ultraviolet radiation effectiveness;
wherein said at least one baffle or airflow interrupter comprises a plurality of quartz tubular members situate in said transparent tubular member.

\* \* \* \* \*

UNITED STATES PATENT AND TRADEMARK OFFICE
CERTIFICATE OF CORRECTION

| | |
|---|---|
| PATENT NO. | : 10,039,854 B2 |
| APPLICATION NO. | : 15/642704 |
| DATED | : August 7, 2018 |
| INVENTOR(S) | : David Louis Kirschman |

Page 1 of 1

It is certified that error appears in the above-identified patent and that said Letters Patent is hereby corrected as shown below:

In the Claims

Column 10, Line 61, Claim 20, delete "16" and insert --19-- therefor.

Signed and Sealed this
Second Day of October, 2018

Andrei Iancu
*Director of the United States Patent and Trademark Office*